United States Patent
Russi et al.

(10) Patent No.: US 10,799,519 B2
(45) Date of Patent: Oct. 13, 2020

(54) REDUCED PRESSURE MAILLARD SYNTHESIS OF CARBOHYDRATE ENERGY SUPPLEMENT FOR RUMINANT LIVESTOCK

(71) Applicant: Rupca LLC, Merced, CA (US)

(72) Inventors: Juan Pablo Russi, Buenos Aires (AR); Paula Figuiera Artieda, Buenos Aires (AR); Alejandro Ramon Castillo, Merced, CA (US)

(73) Assignee: RUPCA LLC, Merced, CA (US)

( * ) Notice: Subject to any disclaimer, the term of this patent is extended or adjusted under 35 U.S.C. 154(b) by 0 days.

(21) Appl. No.: 15/988,629

(22) Filed: May 24, 2018

(65) Prior Publication Data

US 2018/0338990 A1    Nov. 29, 2018

Related U.S. Application Data

(60) Provisional application No. 62/510,360, filed on May 24, 2017.

(51) Int. Cl.
| | | |
|---|---|---|
| *A61K 31/7004* | (2006.01) | |
| *A23K 20/147* | (2016.01) | |
| *A23K 50/15* | (2016.01) | |

(52) U.S. Cl.
CPC ........ *A61K 31/7004* (2013.01); *A23K 20/147* (2016.05); *A23K 50/15* (2016.05)

(58) Field of Classification Search
CPC ... A61K 31/7004; A23K 20/147; A23K 50/15
USPC ......................................................... 514/23
See application file for complete search history.

(56) References Cited

U.S. PATENT DOCUMENTS

| | | | |
|---|---|---|---|
| 3,595,678 A | 7/1971 | Shimazaki et al. | |
| 4,957,748 A | 9/1990 | Winowiski | |
| 5,023,091 A | 6/1991 | Winowiski | |
| 5,064,665 A * | 11/1991 | Klopfenstein | A23K 20/147 426/2 |
| 5,789,001 A | 8/1998 | Klopfenstein et al. | |
| 6,221,380 B1 | 4/2001 | Woodroofe et al. | |
| 6,322,827 B1 | 11/2001 | Scott et al. | |
| 6,506,423 B2 | 1/2003 | Drouillard et al. | |
| 7,303,775 B1 | 12/2007 | Patton et al. | |
| 2006/0039955 A1 | 2/2006 | Messman et al. | |
| 2007/0009502 A1 | 1/2007 | Lall et al. | |
| 2007/0232647 A1 | 10/2007 | Goetze et al. | |
| 2009/0196949 A1 | 8/2009 | Winowiski | |
| 2011/0195146 A1 | 8/2011 | Russi | |
| 2016/0174595 A1 | 6/2016 | Miller et al. | |

FOREIGN PATENT DOCUMENTS

| | | |
|---|---|---|
| CA | 2099529 C | 1/2002 |
| WO | 2005025323 A1 | 3/2005 |

OTHER PUBLICATIONS

Oginni et al. Effect of starch gelatinization and vacuum frying conditions on structure development and associated quality attributes of cassava-gluten based snack. Food Structure 3:12-20, 2015. (Year: 2015).*

Drackley, J. K. "Biology of Dairy Cows During the Transition Period: the Final Frontier?" Journal of Dairy Science 82 (11):2259-2273. (1999). cited byapplicant.

Bell, A. W. "Regulation of organic nutrient metabolism during transition from late pregnancy to early lactation". J Anim Sci 73: 2804-2819. (1999).

Drackley, et al. "Adaptations of Glucose and Long-Chain Fatty Acid Metabolism in Liver of Dairy Cows During the Periparturient Period". Journal of Dairy Science 84(E. Suppl.):E100-E112. (2001).

Wheelock, et al. "Effects of heat stress on energetic metabolism in lactating Holstein cows". Journal of Dairy Science 93(2): 644-655. (2010).

* cited by examiner

*Primary Examiner* — Yih-Horng Shiao
(74) *Attorney, Agent, or Firm* — Fox Rothschild LLP

(57) ABSTRACT

A method of preparing rumen-protected carbohydrates for use in ruminant feeds by inducing the Maillard reaction between a reducing carbohydrate source and a protein source under reduced pressure conditions is disclosed. Products made by the process, and methods for maintaining or restoring blood glucose levels to within the normal reference range for ruminants, especially during transition or under heat stress are also disclosed.

20 Claims, 1 Drawing Sheet

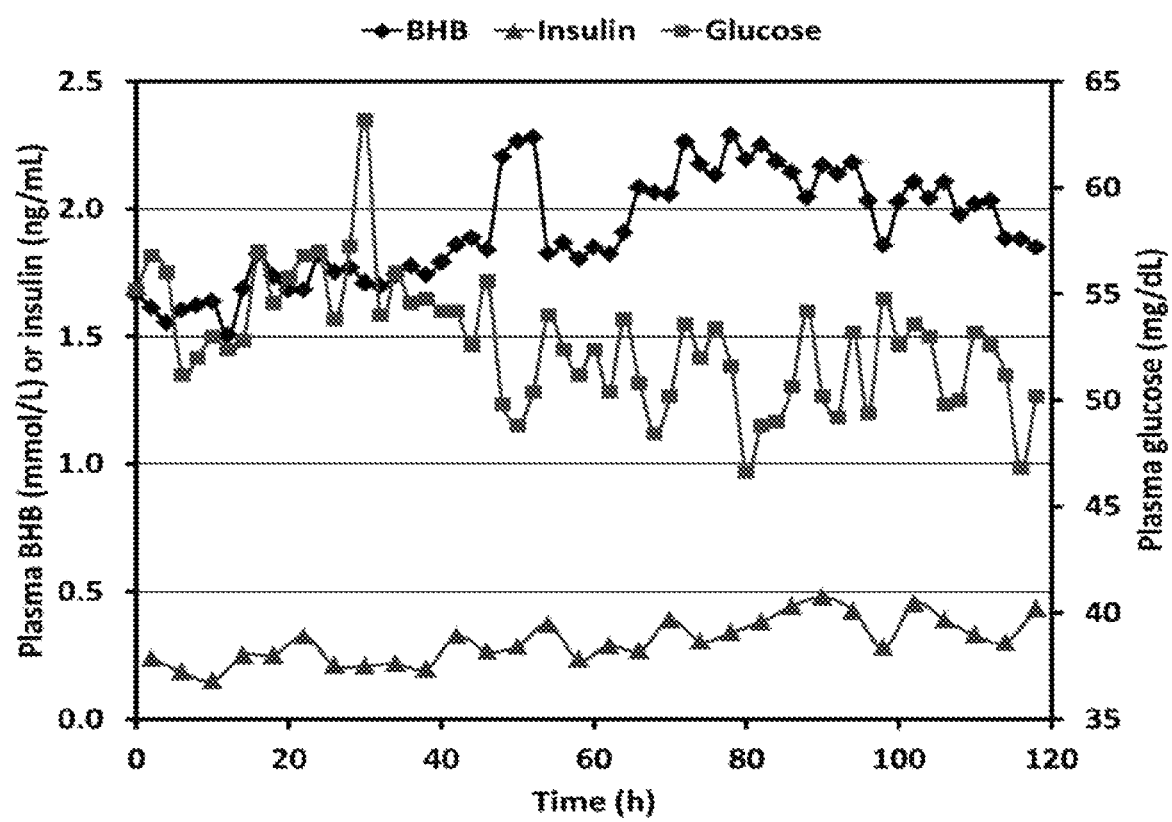

REDUCED PRESSURE MAILLARD SYNTHESIS OF CARBOHYDRATE ENERGY SUPPLEMENT FOR RUMINANT LIVESTOCK

FIELD OF THE INVENTION

The present invention relates to providing ruminant animals a source of high quality rumen-protected carbohydrates (RUPCAs) in the small intestine, for example during the transition period and/or during heat stress and or any kind of stress in ruminants, to increase the ruminant's glucose supply and maintain high milk yield, health and reproduction. In particular, the present invention relates to the preparation of RUPCAs using a reduced pressure Maillard reaction. The invention also relates to a slow release carbohydrate for horses to avoid colic that happens when excess carbohydrates are fed at once. The present invention makes glucose available to the animal as a rumen bypass nutrient to enhance performance and as an aid to the immune system.

BACKGROUND

It is known that during the transition period, which is three weeks before and three weeks after calving, ruminants experience a decrease in glucose levels, with the blood glucose level of cows being particularly low compared to other ruminants. During the transition period, the plasma glucose level drops from 60 to 70 mg/dl to about 45 mg/dl. Moreover, in the first few days after parturition, liver glycogen is depleted (Vasquez-Anon et al., J. Dairy Sci. 77(6), 1521-1528).

Studies have also shown that heat-stressed ruminants experience an increase in glucose demands in skeletal muscle and cerebral metabolism. While heat-stressed ruminants experience a negative energy balance, adipose tissue is not mobilized and there is an increase in insulin sensitivity. This suggests that glucose is the preferred energy source necessary to minimize the negative impact of heat stress in ruminants (Rhodes et al J. Dairy Sci. 92(5), 1986-1997).

U.S. Pat. Nos. 7,303,775 and 6,322,827 disclose carbohydrate ruminant feed energy supplements and methods of use. However, the '775 patent discloses fructose as an energy source, and the methodology to protect the energy source is based on "fat coating." As for the '827 patent, the carbohydrate is disclosed to be chemically treated with formaldehyde to produce a protected carbohydrate.

U.S. Pat. Nos. 4,957,748, 5,789,001 and 6,221,380 disclose the use of Maillard reaction products, but only as a method to produce rumen-inert lipids and proteins. U.S. Pat. No. 8,507,025 discloses an energy supplement for ruminant animals prepared by a Maillard reaction method conducted under positive pressure (1 to 2 atmospheres). Use of carbohydrates is limited to what is necessary to produce protected lipids and proteins. There remains a need for a product that includes a source of high quality rumen protected carbohydrates (RUPCAs) or blood glucose precursor for dairy animals, particularly during the transition period or during heat stress. Further, an industrially acceptable manufacturing method of producing such RUPCAs is desired.

SUMMARY OF THE DISCLOSURE

For an industrially robust process, it has now been unexpectedly discovered that for the preparation of RUPCAs, the Maillard reaction can be conducted by heating under less than atmospheric pressure; i.e. under a vacuum.

The present invention includes methods according to which the product of the present invention is made, as well as products made by the inventive method. As known in the art, when certain foods are heat treated under moist conditions Maillard type reactions can occur. These reactions initially involve a condensation between the carbonyl group of a reducing sugar with the free amino group of an amino acid, protein, urea or other suitable nitrogen source. The result is a Maillard reaction product. The present invention incorporates the discovery that the Maillard reaction, specifically a Maillard reaction conducted at reduced pressure (below atmospheric pressure) under specific conditions, can be advantageously employed to create rumen-protected carbohydrates that can be used as in a ruminant energy feed supplement.

As disclosed herein, a method of preparing a carbohydrate protected from ruminal degradation comprises:
mixing a reducing carbohydrate source and a nitrogen source, where the amount by weight of the reducing carbohydrate source is greater than the amount by weight of the nitrogen source, to provide a mixture; and
heating the mixture for a sufficient amount of time, at a sufficient temperature and under reduced pressure, in the presence of sufficient moisture so that a Maillard reaction product is formed, where the amount of nitrogen source and the heating time, temperature, reduced pressure and moisture conditions are sufficient to provide an amount of a Maillard reaction product effective to prevent ruminal degradation of the carbohydrate.

Optionally, enzymes can be added to enhance the RUPCA reaction. Suitable enzymes include xylanase, β-mannanase, β-glucanase, α-galactosidase, glucose oxidase, cellulase, neutral amylase, acid protease, neutral protease, alkaline protease, and lipase.

The nitrogen source can be a protein with a reactive amino group. The nitrogen source can be a non-protein nitrogen source. The non-protein nitrogen source can be selected from the group consisting of urea or any amino acids; preferred amino acids include glycine, methionine, histidine, glutamine and lysine.

The reducing carbohydrate source can be selected from the group consisting of fructose, sucrose, dextrose, high fructose corn syrup, glucose, lactose, molasses, xylose, and spent sulfite liquor.

The mixture can be heated to a temperature between about 60° C. and about 90° C., or between about 60° C. and about 85° C., or between about 60° C. and about 80° C. The pressure during heating can be between about 0.4 Atm and about 0.7 Atm, or between about 0.4 Atm and about 0.6 Atm, or between about 0.4 Atm and about 0.5 Atm.

The mixture heating time can be about 7 min to about 120 min. The mixture heating time can be about 45 min.

The ratio of reducing carbohydrate to nitrogen source can be about 10:90. The ratio of reducing carbohydrate to nitrogen source can be about 50:50. The ratio of reducing carbohydrate to nitrogen source can be about 90:10.

The method of preparing a carbohydrate protected from ruminal degradation can comprise:
mixing a reducing carbohydrate source and a nitrogen source selected from a protein with a reactive amino group and/or a non-protein nitrogen source to provide a mixture; and
heating the mixture for about 7 min to about 120 min, optionally up to 240 min, at a temperature between about 30° C. and about 135° C., and a pressure between about 0.4 Atm and about 0.7 Atm, in the presence of sufficient moisture so that a Maillard reaction product is formed in an amount sufficient to prevent ruminal degradation of the carbohydrate.

An energy supplement for use in ruminant feed comprises rumen protected carbohydrates prepared by the above-described method. The reducing carbohydrate can range from about 10% to about 90%, or about 20% to about 75% in the final supplement formula.

The energy supplement mixing step can further comprise a pH adjustment agent. The pH adjustment agent can comprise a buffer. The buffer can selected from one or more of sodium bicarbonate, potassium dihydrogen phosphate, dipotassium hydrogen phosphate and sodium hydroxide. The buffer can consist essentially of about 50% sodium bicarbonate, about 20% potassium dihydrogen phosphate, and about 30% dipotassium hydrogen phosphate.

The pH of the energy supplement can be adjusted to about 2 to about 11, preferably about 6.0 to about 8.5.

For the energy supplement the rumen protected carbohydrate can be a liquid product dried onto a matrix. The matrix can be selected from the group consisting of soybean meal, corn meal, silicates, rice hulls, mill run, ground corn, dried corn gluten feed, citrus pulp, oats hulls, sorghum grain, wheat mill run, sunflower meal, wet distillers grains, dry distillers grains aluminum silicates, diatomaceous earths, maltodextrins, maltodextrose, wheat midds and mixtures of two or more thereof.

A method for maintaining or restoring blood glucose levels within the normal reference range for ruminants, comprises feeding an effective amount of the above-described energy supplement to the ruminant. The energy supplement can be fed daily.

A method for treating or preventing heat stress in ruminant animals, comprises feeding an effective amount of the above-described energy supplement to the ruminant animals. The ruminant animals can be selected from dairy cows, beef cows, finishing steers, growing steers, calves and early weaned calves.

A method for treating or preventing stress in ruminant animals induced by shipping and/or handling, comprises feeding an effective amount of the above-described energy supplement to the ruminant animals. The ruminant animals can be selected from calves received in a feedlot, yearlings received in a feedlot, early weaned ruminant animals, and animals prepared for shipping to a slaughterhouse.

A method for treating or preventing stress in ruminant animals in transition, comprises feeding an effective amount of the above-described energy supplement to the ruminant animals, from before calving up to end of lactation. The ruminant animals in transition can be selected from dairy cows or beef cows. The energy supplement can be fed from about 21 days before calving up to about 21 days post calving.

A method for treating cows experiencing fertility problems, comprises feeding an effective amount of the above-described energy supplement to such cows. The cows can be selected from dairy cows and beef cows.

The foregoing and other aspects of the present invention will be better appreciated by reference to the following drawing and detailed description set forth below.

BRIEF DESCRIPTION OF THE DRAWING

FIG. 1 shows a graph of concentrations of β-hydroxybutyrate (BHB), glucose and insulin in blood samples collected once every 2 h from early postpartum Holstein or Guernsey dairy cows that were fed either a control TMR, or a TMR+10% rumen protected carbohydrate, according to Example 1.

DETAILED DESCRIPTION OF EMBODIMENTS

A body of scientific evidence now suggests that a ruminant's metabolism responds to stress by lowering sensitivity of tissues to insulin, allowing it to spare glucose needed by the immune system. It is clear that high producing dairy cows need this mechanism (glucose sparing) in order to channel more resources to the mammary gland. Almost every stressed ruminant model responds this way, including stressed animals sent to a slaughterhouse yielding dark cuts of meat, heat stressed steers, transition dairy cows, and heat stressed high yielding dairy cows. We have demonstrated that feeding rumen-protected glucose actually enhanced insulin concentration in blood plasma and helped the animals to cope with stress, specifically in transition dairy cows, in heat stressed steers, and in receiving feedlot heifers.

For purposes of the present invention, "stress" is defined according to the definition of livestock stress employed by animal physiologists, in which "stress" consists of external body forces that tend to displace homeostasis and "strain" is the internal displacement brought about by stress, wherein there are environmental forces continuously acting upon animals that disrupt homeostasis. See, for example, G. H. Stott, "What is Animal Stress and How is it Measured?," *J Anim Sci.,* 52(1), 150-153 (January 1981).

Further, for the purposes of the present invention, "dark meat" refers to dark, firm and dry (DFD) meat, wherein the carcass meat is darker and drier than normal and has a much firmer texture. The muscle glycogen has been used up during the period of handling, transport and pre-slaughter and as a result, after slaughter, there is little lactic acid production, which results in DFD meat. This meat is of inferior quality, as the less pronounced taste and the dark color is less acceptable to the consumer and has a shorter shelf life due to the abnormally high pH-value of the meat (6.4-6.8). DFD meat means that the carcass was from an animal that was stressed, injured or diseased before being slaughtered.

Without wishing to be bound by any particular theory, it is believed that when a ruminant animal is not stressed, feeding glucose does not enhance milk production or immunity, and most of the excess glucose is utilized by the splanchic and mesenteric tissue which converts glucose into fat. On the other hand, in high producing ruminants, the glucose requirements are not determined or well understood, such as when the animal is stressed and insulin resistance is triggered metabolically. In such cases, glucose reaches the liver and is distributed and used according to the animal body's need, typically first for the immune system, followed by milk production, and then for reproduction. In the first two cases, when insulin resistance is unknown the availability of glucose required to maintain the expected level of milk production or health may not be sufficient; therefore, offering a rumen protected form of glucose is warranted.

The invention also relates to a slow release carbohydrate for horses to avoid colic that happens when excess carbohydrates are fed at once. The invention further relates to preventing dark meat cuts in ruminant animals sent to a slaughterhouse, overcoming fertility problems in ruminants, and overcoming stress issues in receiving feedlot animals.

The energy supplement components of the present invention can be dry fine powders or liquid. The energy supplement can be made by weighing and mixing together the component quantities with up to 25% by weight of distilled water in any equipment suitable for mixing materials. The mixture is then heated under reduced pressure to between about 60 and about 95° C., preferably between about 60 and about 90° C., at a pressure between about 0.4 and less than 1.0 Atm for about 7 minutes to about 2 hours, preferably between about 30 and about 45 minutes, and then cooled to room temperature. The table below indicates the appropriate temperatures and pressures determined to be useful for the reduced pressure Maillard reaction:

| Temperatures C. ° | Pressure in ATM |
|---|---|
| 100 | 1 |
| 95 | 0.83 |
| 90 | 0.70 |
| 85 | 0.59 |
| 80 | 0.51 |
| 75 | 0.46 |
| 70 | 0.44 |
| 65 | 0.44 |
| 60 | 0.44 |

The reaction mixture has a pH ranging between about 2 and about 11, preferably from about 6.0 to about 8.5.

A typical formulation is depicted in Table 1, together with the acceptable ranges within which individual components can be varied:

TABLE 1

| Ingredient | International feed number | Proportion (g/kg) ideal | range |
|---|---|---|---|
| 1. Dextrose | 6-02-633 | 360 | 100-900 |
| 2. Soya bean meal | 5-12-820 | 600 | 0-700 |
| 3. Urea | 6-04-272 | 20 | 10-120 |
| 4. Na bicarbonate | 6-04-272 | 35 | 0-50 |
| 5. $K_2HPO_4$ | 6-02-632 | 6 | 0-10 |
| 6. $KH_2PO_4$ | NA | 4.5 | 0-8 |
| 7. NaOH | NA | 10 | 0-20 |

The energy supplement of the present invention can also be optionally formulated with alternate carbohydrate sources in accordance with availability and pricing of ingredients. Fructose, sucrose, high fructose corn syrup, glucose, lactose, molasses, xylose, and spent sulfite liquor, as well as other reducing sugars can optionally be used as a carbohydrate source in the formulation.

Furthermore, the urea, which is a source of nitrogen, can be optionally exchanged for glycine, peptone, casein hydrolysates, casein, methionine, lysine or another amino acid in accordance with availability and pricing of ingredients.

When the supplement is prepared in a liquid medium, resulting in a liquid product, the resulting liquid product can be applied to and dried onto different matrices, such as soybean meal, corn meal, silicates (verixite, vermiculite, etc.), rice hulls, mill run, ground corn, citrus pulp, oats hulls, sorghum grain, wheat mill run, aluminum silicates, diatomaceous earths, maltodextrins, maltodextrose, dry distillers grains, wet distillers grains, wheat midds, or a blend of two or more of these.

NaOH can be used as an alternative to sodium bicarbonate, $K_2HPO_4$, and $KH_2PO_4$ as a buffer component. Phosphoric acid can also be used as a buffer component.

The energy supplement of the present invention can be conveniently fed to a ruminant admixed with a conventional ruminant feed. Feeds are typically vegetable materials edible by ruminants, such as grass silage, corn silage, legume silage, legume hay, grass hay, corn grain, oats, barley, distiller's grain, brewer's grain, soya bean meal, and cottonseed meal. Concentrates or grains are preferred.

For ruminant animals weighing over 500 kg (e.g., young or adult cows), between about 350 and about 2000 grams per day of the energy supplement should be administered, preferably between about 750 and about 1250 grams, and more preferably about 1000 grams per day. For ruminant animals weighing between about 80 kg and about 300 kg (e.g., young or adult sheep), between about 250 and about 750 grams should be administered, preferably about 500 grams per day. For ruminant animals weighing under 150 kg (e.g., young or adult goats), between about 50 and about 400 grams should be administered, preferably about 200 grams per day. With ruminants under heat stress conditions the preferred dose of the product is between about 0.3 and about 2 kg of the product or more typically, between about 0.5 and about 1 kg of the product per day while they are experiencing heat stress conditions.

The energy supplements are intended to be fed to ruminant animals on a daily basis. Ruminants to which the compositions of the present invention can be fed include cows, goats, sheep, and the like. The period for administration to ruminant animals should be from about one month before calving up to the end of lactation. The preferred administration period for ruminant animals weighing over 500 kg is about one month before calving up to the end of lactation, and more preferably about 20 days before calving to about 30 days after calving. The preferred administration period for ruminant animals weighing between about 80 kg and about 300 kg is about 21 days before calving to the end of lactation, more preferably for about 14 days before calving until about 28 days afterwards. The preferred administration period for ruminant animals weighing under 150 kg is about 14 days before parturition up to the end of lactation, more preferably about 14 days before calving until about 21 days afterwards.

One aspect of the invention is directed to a method of preparing a carbohydrate protected from ruminal degradation, the method comprising:

mixing a reducing carbohydrate source and a nitrogen source, where the amount by weight of the reducing carbohydrate source versus the amount by weight of the nitrogen source ranges from about 10:90 to about 90:10, to provide a mixture; and heating the mixture for a sufficient amount of time, at a sufficient temperature and under reduced pressure, in the presence of sufficient moisture so that a Maillard reaction product is formed, where the amount of nitrogen source and the heating time, temperature, reduced pressure and moisture conditions are sufficient to provide an amount of a Maillard reaction product effective to prevent ruminal degradation of the carbohydrate.

The weight % of the reducing carbohydrate source versus the nitrogen source is about 10:90, or about 20:80, or about 30:70, or about 40:60, or about 50:50, or about 40:60, or about 30:70, or about 20:80, or about 10:90. The ratio of reducing carbohydrate to nitrogen source can be about 10:90. The ratio of reducing carbohydrate to nitrogen source can be about 50:50. The ratio of reducing carbohydrate to nitrogen source can be about 90:10.

The nitrogen source can be a protein with a reactive amino group. The nitrogen source can be a non-protein nitrogen source. The non-protein nitrogen source can be selected from the group consisting of glycine, methionine, lysine, or any amino acid, urea, and mixtures of two or more thereof.

The reducing carbohydrate source can be selected from the group consisting of fructose, sucrose, dextrose, high fructose corn syrup, glucose, lactose, molasses, xylose, spent sulfite liquor, and mixtures of two or more thereof. The reducing carbohydrate source can comprise sucrose, glucose, dextrose, fructose or mixtures of two or more thereof. The reducing carbohydrate source can be dextrose. The reducing carbohydrate source can be sucrose. The reducing carbohydrate source can be glucose. The reducing carbohydrate source can be fructose and/or high fructose corn syrup, or any other reducing carbohydrate.

The mixture is heated to a temperature between about 30° C. and about 135° C. The mixture can be heated to a temperature between about 30° C. and about 95° C., or between about 60° C. and about 90° C., or between about 60° C. and about 85° C., or between about 60° C. and about 80° C. The mixture can be heated to a temperature between about 40° C. and about 95° C., or about 45° C. and about 90° C., or about 50° C. and about 85° C., or about 55° C. and about 80° C., or about 60° C. and about 75° C. The pressure during heating can be between about 0.4 Atm and about 0.9 Atm, or about 0.4 Atm and about 0.8 Atm, or between about 0.4 Atm and about 0.7 Atm, or between about 0.4 Atm and about 0.6 Atm, or between about 0.4 Atm and about 0.5 Atm. The pressure during heating can be about 0.4 Atm, or about 0.45 Atm, or about 0.5 Atm, or about 0.55 Atm, or about 0.6 Atm, or about 0.65 Atm, or about 0.7 Atm, or about 0.75 Atm, or about 0.8 Atm, or about 0.85 Atm, or about 0.9 Atm, or about 0.95 Atm.

The mixture heating time can be about 7 min to about 120 min. The mixture heating time can be about 7 min, or about 10 min, or about 15 min, or about 20 min, or about 25 min, or about 30 min, or about 35 min, or about 40 min, or about 45 min, or about 50 min, or about 55 min, or about 60 min, or about 65 min, or about 70 min, or about 75 min, or about 80 min, or about 85 min, or about 90 min, or about 95 min, or about 100 min, or about 105 min, or about 110 min, or about 115 min, or about 120 min. Alternatively, the mixture heating time can be up to about 240 min, such as about 7 min to about 240 min, or about 150 min, or about 175 min, or about 200 min, or about 225 min, or about 240 min.

Optionally enzymes can be added to enhance the RUPCA reaction. Suitable enzyme enhancers include, for example, proteases and carboxylases. Suitable enzymes can be selected from the group consisting of Xylanase, β-mannanase, β-glucanase α-galactosidase, glucose oxidase, cellulase, neutral amylase, acid protease, neutral protease, alkaline protease, and lipase.

The method of preparing a carbohydrate protected from ruminal degradation can comprise:
  mixing a reducing carbohydrate source and a nitrogen source selected from a protein with a reactive amino group and/or a non-protein nitrogen source to provide a mixture; and
  heating the mixture for about 7 min to about 120 min (alternatively, up to about 240 min), at a temperature between about 30° C. and about 135° C., and a pressure between about 0.4 Atm and about 0.7 Atm, in the presence of sufficient moisture so that a Maillard reaction product is formed in an amount sufficient to prevent ruminal degradation of the carbohydrate.

An energy supplement for use in ruminant feed comprises rumen protected carbohydrates prepared by any of the above-described methods. The reducing carbohydrate can range from about 10% to about 90%, or about 15% to about 85%, or about 15% to about 80%, or about 20% to about 75%, or about 20% to about 70%, in the final supplement formula.

The energy supplement mixing step can further comprise a pH adjustment agent. The pH adjustment agent can comprise a buffer. The buffer components can selected from one or more of sodium bicarbonate, potassium dihydrogen phosphate, dipotassium hydrogen phosphate, sodium hydroxide or phosphoric acid. The buffer can consist essentially of about 50% sodium bicarbonate, about 20% potassium dihydrogen phosphate, and about 30% dipotassium hydrogen phosphate, or 10% sodium hydroxide.

The pH of the energy supplement can be adjusted to about 2 to about 11, about 3 to about 10, about 4 to about 9, about 5 to about 8.5, about 6 to about 8.5, or about 6 to about 8. The pH can be about 2, about 2.5, about 3, about 3.5, about 4, about 4.5, about 5, about 5.5, about 6, about 6.5, about 7, about 7.5, about 8, about 8.5, about 9, about 9.5, or about 10, about 10.5, or about 11.

For the energy supplement the rumen protected carbohydrate can be a liquid product dried onto a matrix. The matrix can be selected from the group consisting of soybean meal, corn meal, silicates, rice hulls, mill run, ground corn, citrus pulp, oats hulls, sorghum grain, maltodextrose, maltodextrins, aluminum silicates, diatomaceous earths, wheat mill run, wheat midds, and mixtures of any two or more thereof.

A method for maintaining blood glucose levels within the normal reference range for ruminants comprises feeding an effective amount of the above-described energy supplement to the ruminant. The energy supplement can be fed daily. A method for restoring blood glucose levels within the normal reference range for ruminants comprises feeding an effective amount of the above-described energy supplement to the ruminant. The energy supplement can be fed daily.

A method for treating heat stress in ruminant animals comprises feeding an effective amount of the above-described energy supplement to the ruminant animals. The ruminant animals can be selected from dairy cows, beef cows, finishing steers, growing steers, calves and early weaned calves. A method for preventing heat stress in ruminant animals comprises feeding an effective amount of the above-described energy supplement to the ruminant animals. The ruminant animals can be selected from dairy cows, beef cows, finishing steers, growing steers, calves and early weaned calves.

A method for treating stress in ruminant animals induced by shipping and/or handling comprises feeding an effective amount of the above-described energy supplement to the ruminant animals. The ruminant animals can be selected from calves received in a feedlot, yearlings received in a feedlot, early weaned ruminant animals, and animals prepared for shipping to a slaughterhouse. A method for preventing stress in ruminant animals induced by shipping and/or handling comprises feeding an effective amount of the above-described energy supplement to the ruminant animals. The ruminant animals can be selected from calves received in a feedlot, yearlings received in a feedlot, early weaned ruminant animals, and animals prepared for shipping to a slaughterhouse.

A method for producing fewer dark meat cuts from ruminant animals sent to a slaughterhouse comprises treating or preventing stress in the animals by feeding an effective amount of the energy supplement of the above-described energy supplement to the ruminants. The ruminant animals can be selected from calves, yearlings, and steers received in a feedlot.

A method for treating stress in ruminant animals in transition comprises feeding an effective amount of the above-described energy supplement to the ruminant animals, from before calving up to end of lactation. The ruminant animals in transition can be selected from dairy cows or beef cows. The energy supplement can be fed from about 21 days before calving up to about 21 days post calving. A method for preventing stress in ruminant animals in transition comprises feeding an effective amount of the above-described energy supplement to the ruminant animals, from before calving up to end of lactation. The ruminant animals in transition can be selected from dairy cows or beef cows. The energy supplement can be fed from about 21 days before calving up to about 21 days post calving.

A method for treating cows experiencing fertility problems, comprises feeding an effective amount of the above-described energy supplement to such cows. The cows can be selected from dairy cows and beef cows.

EXAMPLES

In the following examples the RUPCA was prepared by heating at a temperature of 85 to 95° C. for 2 to 4 hours under low pressure (0.80 to 0.95 Atm).

Example 1: Short-Term Feeding of a Rumen-Protected Carbohydrate Increases Plasma Insulin Concentrations in Early Postpartum Dairy Cows Low blood glucose concentrations early postpartum are associated with low blood insulin concentrations, postpartum metabolic disorders, and infertility. The hypothesis was that short-term feeding of a rumen protected carbohydrate (RUPCA; 56% soybean meal, 40% soluble carbohydrates, 3.2% urea, and 0.8% minerals) would increase blood insulin concentrations by increasing glucose supply from the gastrointestinal tract. Lactating dairy cows (4 Holstein and 1 Guernsey; 17±2 DIM; 30.9±4.6 kg milk and 13.7±2.6 kg DMI per day) were jugular catheterized, barn housed, and milked 2X. During the first 24 h (day 1), cows were fed a nutritionally balanced TMR (corn silage, haylage, wet brewer grains, dry corn, alfalfa hay, rumen protected and unprotected soybean meal, soyhulls, and premix). After 24 h (d 2, 3, and 4), cows were fed the TMR with the RUPCA added at 10% of diet DM. On d 5 cows were switched to control TMR. Blood was sampled every 2 h through a jugular catheter. Plasma was isolated and analyzed for insulin, glucose, BHB and nonesterified fatty acids (NEFA). There was an effect of day (P<0.001) on plasma insulin concentrations (0.23, 0.24, 0.31, 0.40, and 0.36 ng/mL; standard error of the mean (SEM)=0.027; d 1 to 5, respectively). The increase in blood insulin was associated with a decrease in plasma glucose (54.4, 55.7, 51.0, 50.9, and 51.3 mg/dL; SEM=0.7; d 1 to 5) and an increase (P<0.001) in plasma BHB (1.64, 1.78, 2.01, 2.19, and 1.97 mmol/L; SEM=0.06; d 1 to 5; P<0.001). There was no effect of day on plasma NEFA but there was an effect of time (P<0.001). Lowest plasma NEFA concentrations were at 1200 h (314±29 µEq/L). The maximum NEFA concentrations were at 0600 h (641±29 µEq/L) and 1800 h (575±29 µEq/L) in samples collected immediately before fresh feed in the morning and afternoon (respectively).

In conclusion, short-term feeding of the RUPCA increased blood insulin concentrations. The increase in blood insulin was associated with a decrease in blood glucose and an increase in BHB. Feeding RUPCA to early postpartum dairy cows effectively alleviated depressed insulin and shifted associated metabolite concentrations. As shown in FIG. 1, Concentrations of β-hydroxybutyrate (BHB; standard error of the mean (SEM)=0.2; ⊒), glucose (SEM=2.2; ■) and insulin (SEM=0.07; ▲) in blood samples collected once every 2 h from early postpartum Holstein (n=4) or Guernsey (n=1) dairy cows that were fed either a control TMR (0 to 24 h and 96 to 120 h) or a TMR+10% rumen protected carbohydrate (RUPCA; 24 to 96 h).

Example 2: Physiologic Responses to Feeding Rumen-Protected Glucose (RUPCA) to Lactating Dairy Cows We hypothesized that supplementing RUPCA would increase concentrations of glucose and insulin resulting in decreased activity of liver cytochromes P450 2C and P450 3A, thus increasing blood progesterone. Estrus and ovulation were synchronized in 62 Holstein cows using GnRH and $PGF_{2\alpha}$, (d 0=ovulation). Cows were milked thrice daily and assigned randomly to be fed individually a TMR supplemented with 0, 1, 2, or 4 kg of a RUPCA product top-dressed into the diet beginning on d −3. Blood was collected pre-feeding and 8 h after feeding on d 0, 2, and 4 to determine concentrations of glucose and insulin concentrations and daily from d 2 through 12 to assess progesterone. Blood was collected every 4 h for 24 h on d 8 to assess a circadian pattern in progesterone. Diameter of the corpus luteum (CL) was determined by ultrasonography on d 10. On d 8, feed intake (FI; P=0.68), ECM (P=0.72), ECM:FI (P=0.52), somatic cell count (P=0.64) and percentages of milk fat (P=0.56) and lactose (P=0.81) did not differ among treatments. Milk percentages of protein differed (P=0.01) among treatments and percentages milk solids (P=0.04) and protein (P=0.004) decreased linearly with increasing dose of RUPCA. Neither pre-feeding (P=0.42) nor post-feeding (P=0.57) concentrations of glucose differed among treatments; however, post-feeding glucose decreased (P=0.01) from d 0 through 4. Pre-feeding insulin (P=0.35) did not differ among treatments, but a post-feeding quadratic (P=0.06) response of insulin was detected among treatments. Volume of the CL on d 10 did not differ (P=0.49) among treatments. Milk urea nitrogen increased linearly (P<0.001) with dose and pregnancy risk at first AI decreased linearly (P=0.01) with increasing dose. Concentrations of progesterone increased (P<0.01) from d 2 to 11 but were unaffected by treatment (P=0.77). The pattern of progesterone on d 8 fit a $4^{th}$-order polynomial curve ($R^2$=0.97) with all concentrations during the 24-h period differing (P<0.05) from the last sample concentration. We conclude that the rumen-protected glucose product did not affect progesterone concentrations. Results are shown in Table 1.

TABLE 1

| RUPCA | 0 kg | 1 kg | 2 kg | 4 kg |
| --- | --- | --- | --- | --- |
| Feed intake, kg/d | 45.6 ± 1.6 (15) | 46.3 ± 1.6 (15) | 44.5 ± 1.6 (15) | 47.1 ± 1.5 (16) |
| ECM, kg/d | 47.8 ± 1.1 (15) | 49.5 ± 1.1 (15) | 48.9 ± 1.1 (15) | 49.0 ± 1.1 (16) |

TABLE 1-continued

| RUPCA | 0 kg | 1 kg | 2 kg | 4 kg |
|---|---|---|---|---|
| ECM:FI | 1.07 ± 0.03 (15) | 1.09 ± 0.03 (15) | 1.13 ± 0.03 (15) | 1.09 ± 0.03 (16) |
| Milk fat, % | 3.78 ± 0.15 (15) | 3.90 ± 0.15 (15) | 4.03 ± 0.15 (15) | 4.05 ± 0.15 (16) |
| Milk protein | 2.75 ± 0.05 (15) | 2.63 ± 0.05 (15) | 2.69 ± 0.05 (15) | 2.53 ± 0.05 (16) |
| Milk lactose | 5.05 ± 0.04 (15) | 5.06 ± 0.04 (15) | 5.01 ± 0.04 (15) | 5.03 ± 0.04 (16) |
| MUN, mg/dL | 15.1 ± 0.6 (15) | 16.3 ± 0.6 (15) | 17.8 ± 0.6 (15) | 20.7 ± 0.6 (16) |
| Insulin, µg/L | 0.40 ± 0.03 | 0.31 ± 0.03 | 0.34 ± 0.03 | 0.38 ± 0.03 |
| Glucose, mg/dL | 61.8 ± 2.9 (15) | 62.4 ± 2.9 (15) | 65.6 ± 2.8 (15) | 66.2 ± 2.8 (16) |
| CL volume, cm$^3$ | 9.5 ± 2.2 (13) | 10.2 ± 2.1 (15) | 9.2 ± 2.1 (15) | 13.4 ± 2.1 (16) |
| Pregnancy risk, % | 69.2 (13) | 14.3 (14) | 42.9 (14) | 25.0 (16) |

Example 3: Effect of Rumen Protected Carbohydrate Supplementation on Performance in Feedlot Finishing Steers During Heat Stress Finishing steers during the summer can be challenging due to the effects of high temperatures and humidity on DMI. The objective of this study was to evaluate the inclusion of a rumen-protected carbohydrate (RUPCA) (U.S. Pat. No. 8,507,025) on performance of finishing steers during heat stress. Temperature-humidity index average measured every day during the experiment was 72±4.9. Crossbred steers (n=135; 355±20 kg) were used in a 62-d experiment. Steers were blocked by initial BW and placed into 15 pens. Steers within blocks were randomly assigned to 3 treatments: T0=fed 91.4% of a basal diet (% DM), 22.3% corn silage, 65.9% dry corn, 0.6% sunflower meal, 0.5% urea, 2% minerals and vitamins and 8.6% of a supplement containing (% DM) 58.1% soybean meal, 38.9% soluble carbohydrates, 2% urea and 1% minerals salts; T1=fed the basal diet plus 4.3% supplement and 4.3% RUPCA; and T2=fed basal diet plus 8.6% RUPCA. The supplement and RUPCA consisted of the same ingredients, differing on the processing of the carbohydrate (i.e., protected or not from ruminal degradation). Body weight was measured on d 0, 15, 39 and 62 relative to the beginning of treatments feeding (d 0). Pen DMI was measured on d 10, 18, 25, 31, 35, 46, 51, 56, 60 and 62. Back-fat on the 12th rib (BF) and LM area were measured on d 1 and 62. Data were analyzed as a randomized complete block design with repeated measures using a mixed model of SAS. Initial BW was used as a covariate. There were no differences between treatments on final BW, BF or LM area on d 62 (P>0.10). Treatment×day interactions were observed for G:F, ADG and DMI (P<0.05) suggesting a different response to treatments during periods of heat stress (Table 2). Feeding RUPCA may be beneficial for finishing steers under heat stress.

Example 4: Effect of Rumen-Protected Carbohydrate Supplementation on Blood and Plasma Metabolites in Finishing Steers During Heat Stress Finishing steers during the summer can be challenging due to the effects of high temperatures and humidity on DMI. The objective of this study was to evaluate the inclusion of a rumen-protected carbohydrate (RUPCA) (U.S. Pat. No. 8,507,025) on blood metabolites of finishing steers during heat stress. Temperature humidity Index average measured every day during the experiment was 72±4.9. Crossbred steers (n=135; 355±20 kg) were used in a 62-d experiment. Steers were blocked by initial BW and placed into 15 pens. Steers within blocks were randomly assigned to 3 treatments. T0) fed 91.4% of a basal diet (% DM), 22.3% corn silage, 65.9% dry corn, 0.6% sunflower meal, 0.5% urea, 2% minerals and vitamins and 8.6% of a supplement containing (% DM) 58.1% soybean meal, 38.9% soluble carbohydrates, 2% urea and 1% minerals salts, T1) fed the basal diet plus 4.3% supplement and 4.3% RUPCA and T2) fed basal diet plus 8.6% RUPCA. The supplement and RUPCA consisted of the same ingredients, differing on the processing of the carbohydrate (i.e., protected or not from ruminal degradation). Blood samples were taken from jugular vein prior morning feeding on d 0, 15, 39, and 62 and analyzed for glucose, insulin, urea and NEFA concentrations. Data were analyzed as a randomized complete block design with repeated measures using a mixed model of SAS. Initial body weight was used as a covariate. Treatment×day interactions were found for insulin (P=0.01) and urea (P=0.02) plasma concentrations. There were no differences on plasma concentration of insulin, NEFA or urea among treatments (P>0.10). T0 showed higher blood glucose concentration (P=0.05). The results suggest that including RUPCA might help to mitigate the negative effects of heat stress on blood metabolites, potentially improving animal performance. Results are shown in Table 3.

TABLE 2

| | Treatment | | | | P-value | | |
|---|---|---|---|---|---|---|---|
| Item | T0 | T1 | T2 | SEM | Trt | Day | Trt × Day |
| DMI, kg/d | 9.9$^{ab}$ | 9.8$^a$ | 10.0$^b$ | 0.07 | 0.04 | <0.001 | 0.001 |
| Initial BW, kg | 287 | 285 | 285 | 0.6 | 0.23 | — | — |
| Final BW, kg | 352 | 357 | 353 | 3.1 | 0.51 | — | — |
| ADG, kg | 1.00 | 1.11 | 1.07 | 0.065 | 0.38 | <0.001 | 0.039 |
| G:F | 0.105 | 0.116 | 0.109 | 0.0051 | 0.32 | <0.001 | 0.004 |
| Backfat 12th rib (62 d), mm | 0.58 | 0.61 | 0.60 | 0.017 | 0.68 | — | — |
| LM area (62 d), cm$^2$ | 57.6 | 54.9 | 56.1 | 0.97 | 0.30 | — | — |

$^{ab}$Means without common superscript differ (P < 0.05)

TABLE 3

| Item | T0 | T1 | T2 | SEM | P-value Trt | Day | Trt × day |
|---|---|---|---|---|---|---|---|
| Glucose, mg/dL | 89.4[a] | 81.9[b] | 83.5[b] | 2.73 | 0.05 | <0.0001 | 0.35 |
| Insulin, μg/dL | 0.56 | 0.73 | 0.68 | 0.072 | 0.35 | 0.0014 | 0.01 |
| NEFA mM | 184.4 | 191.3 | 160.8 | 17.15 | 0.43 | <0.0001 | 0.49 |
| UREA, mg/dL | 25.8 | 26.1 | 22.0 | 0.029 | 0.21 | <0.0001 | 0.02 |

[a,b]Means without common superscript differ (P < 0.05)

Example 5: Effect of Rumen-Protected Carbohydrate Supplementation on Performance, Blood and Plasma Metabolites in Growing Heifers The objective of this study was to evaluate the inclusion of a rumen-protected carbohydrate (RUPCA) on performance, blood and plasma metabolites in growing heifers. Crossbred heifers (n=135; 136±14 kg) were used in an 84-d experiment. Heifers were blocked by initial BW, placed into 15 pens and fed a diet comprised of (DM basis) 38.8% corn silage, 41.5% dry corn, 2% minerals and vitamins mix, and 17.7% supplement or RUPCA, which varied depending on treatments. The supplement and RUPCA consisted of the same ingredients (58.1% soybean meal, 38.9% soluble carbohydrates, 2% urea and 1% mineral salt), differing in the processing of the carbohydrate (i.e., protected or not from ruminal degradation). Heifers within blocks were randomly assigned to 3 treatments: T0) 17.7% supplement (100% unprotected carbohydrate), T1) 8.85% supplement and 8.85% RUPCA, and T2) 17.7% RUPCA (100% protected carbohydrate). Body weight was measured on d 0, 21, 42, 63, and 84. Pen DMI was measured weekly from d 21 to 84. Blood samples were taken on d 0, 42, 63, and 84 from jugular vein prior morning feeding and analyzed for glucose, insulin, urea and NEFA concentrations. Data were analyzed as a randomized complete block design with repeated measures using a mixed model of SAS. Treatment×day interaction were found for DMI (P=0.02), ADG (P<0.0001) and G:F (P<0.0001) and with T1 having the lowest DMI (P<0.05) and the greatest G:F (P<0.05). No differences were found in the concentrations of blood glucose (P>0.91), plasma insulin (P=0.82), plasma NEFA (P=0.802) or plasma urea (P=0.336). Feeding RUPCA to growing heifers improved G:F through lower DMI without altering ADG, blood or plasma metabolites. Results are shown in Table 5.

TABLE 5

| Item | T0 | T1 | T2 | SEM | P-value Trt | Day | Trt × day |
|---|---|---|---|---|---|---|---|
| DMI, kg/d | 6.9[a] | 5.9[b] | 6.8[a] | 0.06 | <0.0001 | <0.0001 | 0.02 |
| ADG, kg | 1.18 | 1.13 | 1.19 | 0.027 | 0.21 | <0.0001 | <0.0001 |
| G:F | 0.161[b] | 0.202[a] | 0.177[ab] | 0.0103 | 0.0003 | <0.0001 | <0.0001 |
| Glucose, mg/dL | 90.2 | 91.6 | 91.2 | 3.52 | 0.91 | <0.0001 | 0.92 |
| Insulin, μg/dL | 0.26 | 0.26 | 0.24 | 0.053 | 0.82 | 0.016 | 0.72 |
| NEFA, mM | 200.8 | 187.9 | 181.3 | 18.74 | 0.54 | 0.0025 | 0.42 |
| Urea, mg/dL | 14.9 | 13.4 | 14.8 | 1.03 | 0.36 | <0.0001 | 0.39 |

[a,b]Means without common superscript differ (P < 0.05)

Example 6: Lactation Performance and Energetic Metabolism of Transition Cows Fed Rumen Protected Glucose Carbohydrate supply and availability in the small intestine may limit milk production in transition dairy cows. Thus, experimental objectives were to evaluate the effects of rumen protected glucose (RUPCA) on milk production and post-absorptive metabolism in transition dairy cows. Fifty-two multiparous cows were blocked by previous 305ME and randomly assigned to one of two iso-energetic and iso-nitrogenous treatments: 1) control diet (CON, n=26) or 2) a diet containing RUPCA (RUPCA, pre-fresh 8.4% RUPCA DM basis, post-fresh 9.5% RUPCA DM basis; n=26). Cows received their respective dietary treatments from d −21 to 28 relative to calving via individual feeding gates. Weekly BW, BCS, milk samples and fecal pH were recorded until 28 DIM, whereas milk yield was recorded through 105 DIM. Blood samples were collected on d −7, 3, 7, 14 and 28 relative to calving. Data were analyzed using repeated measures in the MIXED procedure of SAS. Fecal pH was similar (P=0.87) amongst treatments; however, compared to pre-calving, both treatments had a reduction in pH following calving (7.2 vs 6.6; P<0.01). Milk yield was similar amongst treatments (P=0.37) for 1 to 28 DIM (42.8±1.2 kg/d), as well as through 105 DIM (P=0.92; 47.3±1.3 kg/d). Dry matter intake pre-calving (12.0±0.7 kg/d) and post-calving (22.0±0.7 kg/d) were unaffected by treatment (P>0.65). Milk fat, protein and lactose were similar amongst treatments (P>0.40; 4.36±0.13%, 3.66±0.11% and 4.73±0.06%, respectively). Plasma concentration of BUN and glucose were similar (P>0.57) amongst treatments; however, post-partum concentration of circulating BHBA tended (P=0.13) to be 0.24 mmol/L lower with a concomitant reduction (P<0.01) in NEFA concentration in the RUPCA-fed cows compared to CON (630 vs. 456±68 μEq/L). Circulating insulin tended to be increased (P=0.06; 27%) in RUPCA-fed cows compared with CON. Based upon circulating hormones and metabolites, it appears that treatment influenced energy partitioning pathways in the periparturient period such that RUPCA-fed cows mobilized less adipose tissue compared to the control cows while maintaining milk yield.

What is claimed is:

1. A method of preparing an energy supplement, for use in ruminant feed, comprising a carbohydrate protected from ruminal degradation, said method comprising:

forming a mixture consisting of water, a reducing sugar in the carbohydrate and a nitrogen source selected from the group consisting of proteins with reactive amino groups, urea, and amino acids, wherein the amount by weight of the reducing sugar relative to the nitrogen source is from 100 wt % up to about 900 wt %; and heating said mixture for a sufficient amount of time, at a sufficient temperature and below atmospheric pressure, in the presence of sufficient moisture so that a Maillard reaction product is formed, wherein:

the amount of nitrogen source and the heating time, temperature, pressure and moisture conditions are sufficient to provide a Maillard reaction product, thereby protecting said reducing sugar against ruminal degradation and against degradation of the product until it reaches the small intestine; and between about 20 wt % and about 90 wt % of the final energy supplement formula consists of said reducing sugar.

2. The method of claim 1, wherein the method comprises:
heating said mixture for about 7 min to about 240 min, at a temperature between about 30° C. and about 135° C., and pressure between about 0.4 Atm and about 0.90 Atm, in the presence of sufficient moisture so that a Maillard reaction product is formed in an amount sufficient to prevent ruminal degradation of said sugar.

3. The method of claim 1, where the nitrogen source is a protein with a reactive amino group.

4. The method of claim 1, wherein the nitrogen source is selected from the group consisting of urea and amino acids.

5. The method of claim 4, wherein said amino acid is selected from the group consisting of glycine, methionine, and lysine.

6. The method of claim 1, wherein the mixture is heated to a temperature between about 60° C. and about 85° C. at a pressure between about 0.4 Atm and about 0.9 Atm.

7. The method of claim 6, wherein the mixture is heated to a temperature between about 60° C. and about 80° C. at a pressure between about 0.4 Atm and about 0.5 Atm.

8. The method of claim 7, wherein the heating time is about 45 min.

9. The method of claim 1, wherein the amount by weight of reducing sugar relative to the nitrogen source is about 900 weight percent.

10. An energy supplement comprising rumen protected carbohydrates for use in ruminant feed prepared by the method according to claim 1.

11. A method for treating or overcoming stress in ruminant animals induced by shipping and/or handling, comprising feeding an effective amount of the energy supplement of claim 10 to said ruminant animals.

12. The method of claim 11, wherein said ruminant animals are selected from the group consisting of calves received in a feedlot, yearlings received in a feedlot, early weaned ruminant animals, and animals prepared for shipping to a slaughterhouse.

13. A method for producing fewer dark meat cuts from ruminant animals sent to a slaughterhouse, comprising treating or overcoming stress in said animals by feeding an effective amount of the energy supplement of claim 10 to produce the fewer dark meat cuts after feeding.

14. The method of claim 13, wherein said ruminant animals are selected from the group consisting of calves, yearlings, and steers received in a feedlot.

15. A method for treating cows experiencing fertility problems, comprising feeding an effective amount of the energy supplement of claim 10 to said cows.

16. The method of claim 1, wherein said reducing sugar comprises glucose.

17. The method of claim 1, wherein said mixture is heated for about 7 min to about 120 min.

18. The method of claim 1, wherein the final energy supplement formula consists of about 20 wt % to about 85 wt % of the reducing sugar.

19. The method of claim 18, wherein the final energy supplement formula consists of about 40 wt % to about 75 wt % of the reducing sugar.

20. The method of claim 1, wherein the finally energy supplement formula comprises a buffer.

* * * * *